United States Patent
Inoue et al.

(10) Patent No.: US 11,708,224 B2
(45) Date of Patent: Jul. 25, 2023

(54) CONVEYING APPARATUS AND METHOD

(71) Applicant: ZUIKO CORPORATION, Osaka (JP)

(72) Inventors: Daisuke Inoue, Osaka (JP); Natsuki Ikeda, Osaka (JP)

(73) Assignee: ZUIKO CORPORATION, Osaka (JP)

(*) Notice: Subject to any disclaimer, the term of this patent is extended or adjusted under 35 U.S.C. 154(b) by 71 days.

(21) Appl. No.: 17/614,012

(22) PCT Filed: May 29, 2020

(86) PCT No.: PCT/JP2020/021290
§ 371 (c)(1),
(2) Date: Nov. 24, 2021

(87) PCT Pub. No.: WO2020/250710
PCT Pub. Date: Dec. 17, 2020

(65) Prior Publication Data
US 2022/0219913 A1    Jul. 14, 2022

(30) Foreign Application Priority Data

Jun. 11, 2019    (JP) ................................. 2019-108546

(51) Int. Cl.
*B65G 47/84*    (2006.01)
*A61F 13/15*    (2006.01)
(Continued)

(52) U.S. Cl.
CPC ...... *B65G 47/846* (2013.01); *A61F 13/15764* (2013.01); *B65G 47/248* (2013.01);
(Continued)

(58) Field of Classification Search
CPC .......... A61F 13/15764; A61F 13/15747; A61F 13/15739; B65G 47/248; B65G 47/846; B65G 47/32; B65G 47/28; B65G 47/847
(Continued)

(56) References Cited

U.S. PATENT DOCUMENTS 4,261,457 A * 4/1981 van Maanen ........ B65G 47/846
                                                      198/722
6,511,065 B1 * 1/2003 Cote ..................... B65H 29/06
                                                      198/470.1
(Continued)

FOREIGN PATENT DOCUMENTS

EP          1245513    * 10/2002    ............. B65G 47/84
JP       2010-530269 A    9/2010
(Continued)

OTHER PUBLICATIONS

International Search Report for corresponding Application No. PCT/JP2020/021290, dated Aug. 25, 2020.

*Primary Examiner* — James R Bidwell
(74) *Attorney, Agent, or Firm* — Renner. Otto, Boisselle & Sklar, LLP

(57) ABSTRACT

A conveying method includes first and second pads conveying workpieces with speeds of the first and second pads being varied; circumferential velocities of the first pads and the second pads are accelerated by variable speed mechanisms; the first and second pads move and separate in a state in which a distance between the first pad and the second pad, whose speeds were increased, is increased; the circumferential velocities of the first pads and the second pads are decelerated by the variable speed mechanisms; and a first slider and a second slider, which were subjected to deceleration, overlap each other in a part in a circumferential direction, which causes the first pad and the second pad to approach each other, and the first pad and the second pad move and approach each other in this state in which the first pad and the second pad have approached each other.

16 Claims, 7 Drawing Sheets

(51) Int. Cl.
*B65G 47/32* (2006.01)
*B65G 47/86* (2006.01)
*B65G 47/248* (2006.01)
*B65G 47/28* (2006.01)

(52) U.S. Cl.
CPC .......... *B65G 47/32* (2013.01); *B65G 47/847* (2013.01); *B65G 47/28* (2013.01); *B65G 2811/095* (2013.01)

(58) Field of Classification Search
USPC ...................................... 198/459.8
See application file for complete search history.

(56) References Cited

U.S. PATENT DOCUMENTS

| | | | |
|---|---|---|---|
| 6,730,189 B1 * | 5/2004 | Franzmann | A61F 13/15756 156/519 |
| 9,968,491 B2 * | 5/2018 | Piantoni | A61F 13/15634 |
| 10,206,822 B2 * | 2/2019 | Inoue | A61F 13/15764 |
| 2002/0112929 A1 * | 8/2002 | Koshak | B66B 5/04 188/67 |
| 2004/0245069 A1 * | 12/2004 | Hook | B65G 47/848 198/377.04 |
| 2010/0192739 A1 | 8/2010 | Piantoni | |
| 2018/0256409 A1 | 9/2018 | Inoue | |
| 2019/0247240 A1 | 8/2019 | Tsujimoto | |

FOREIGN PATENT DOCUMENTS

| | | | |
|---|---|---|---|
| WO | 2017/056952 A1 | 4/2017 | |
| WO | 2018/011905 A1 | 1/2018 | |

\* cited by examiner

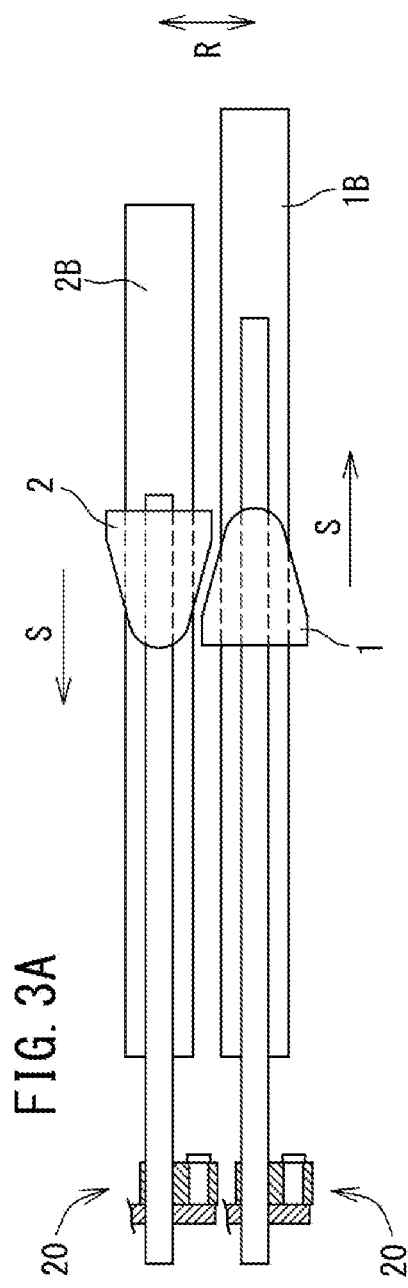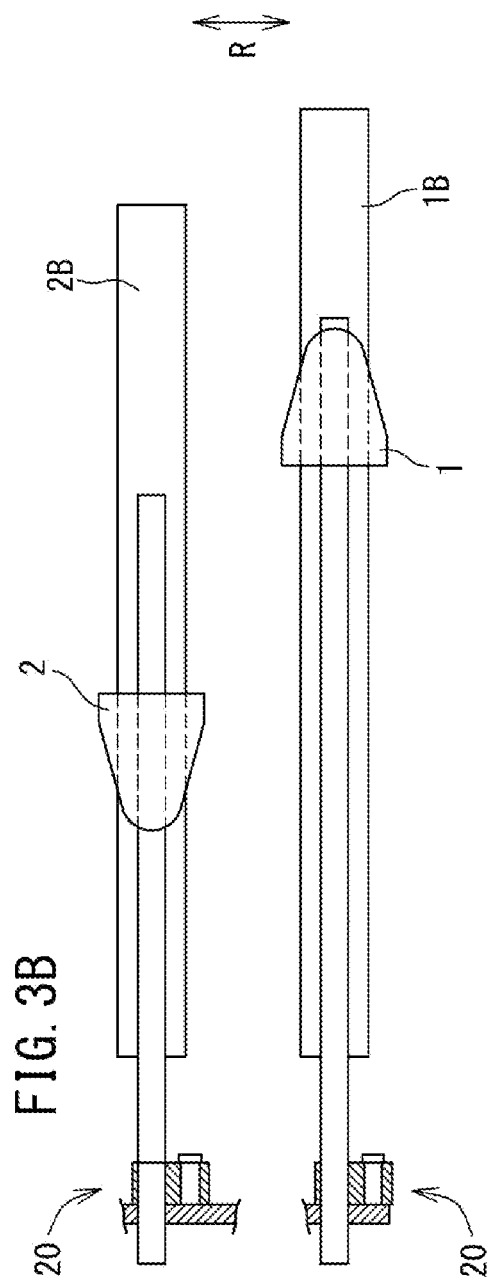

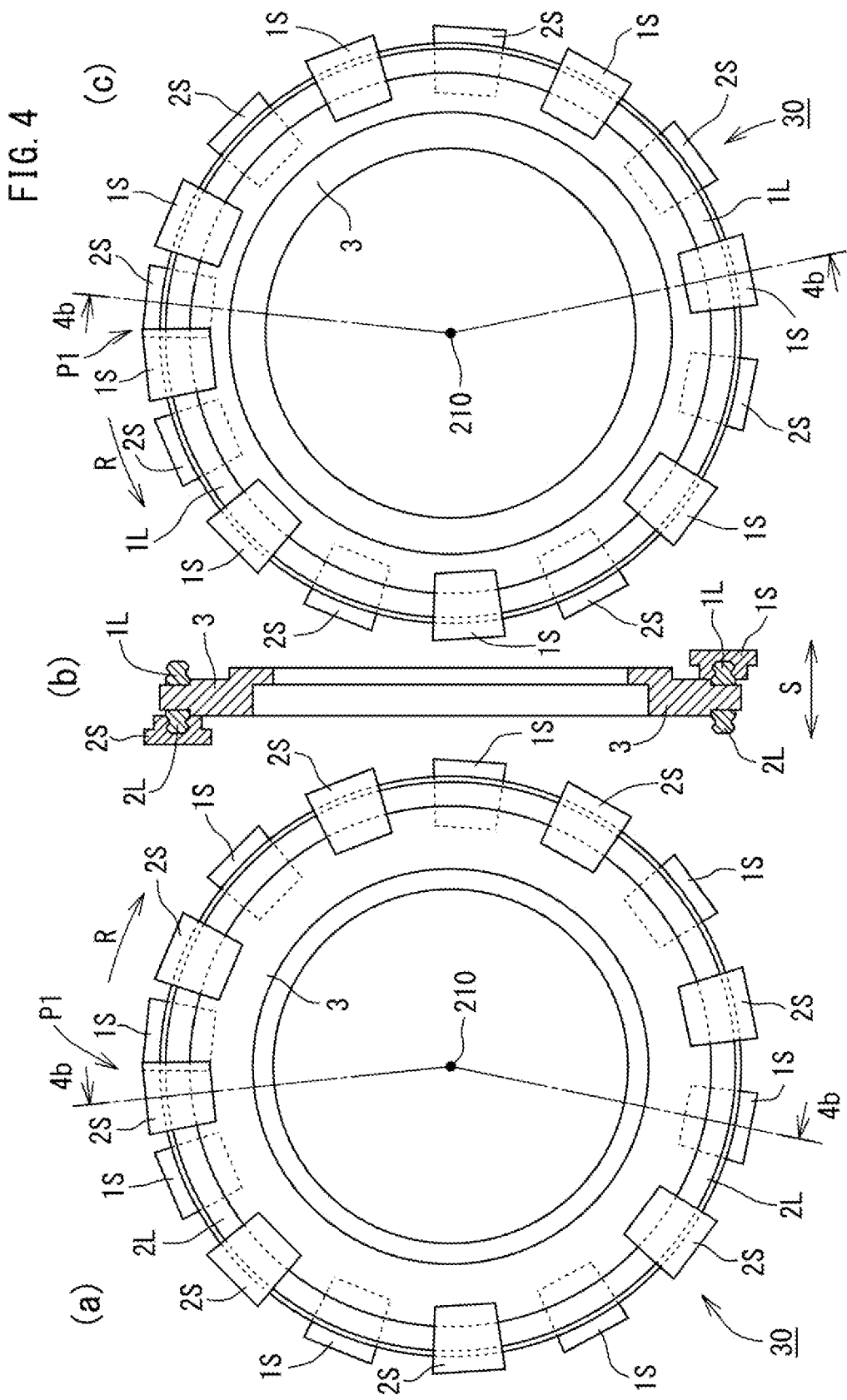

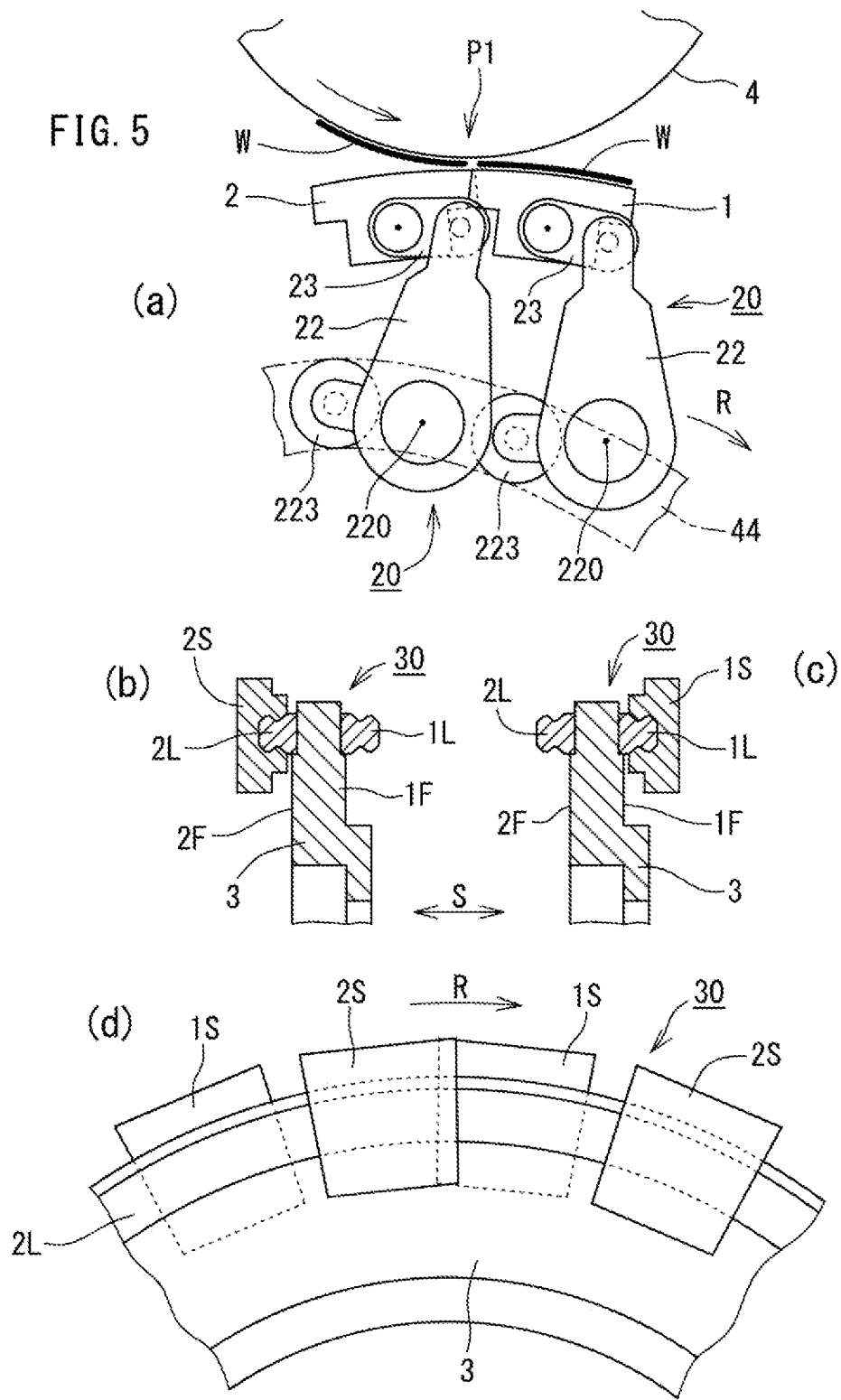

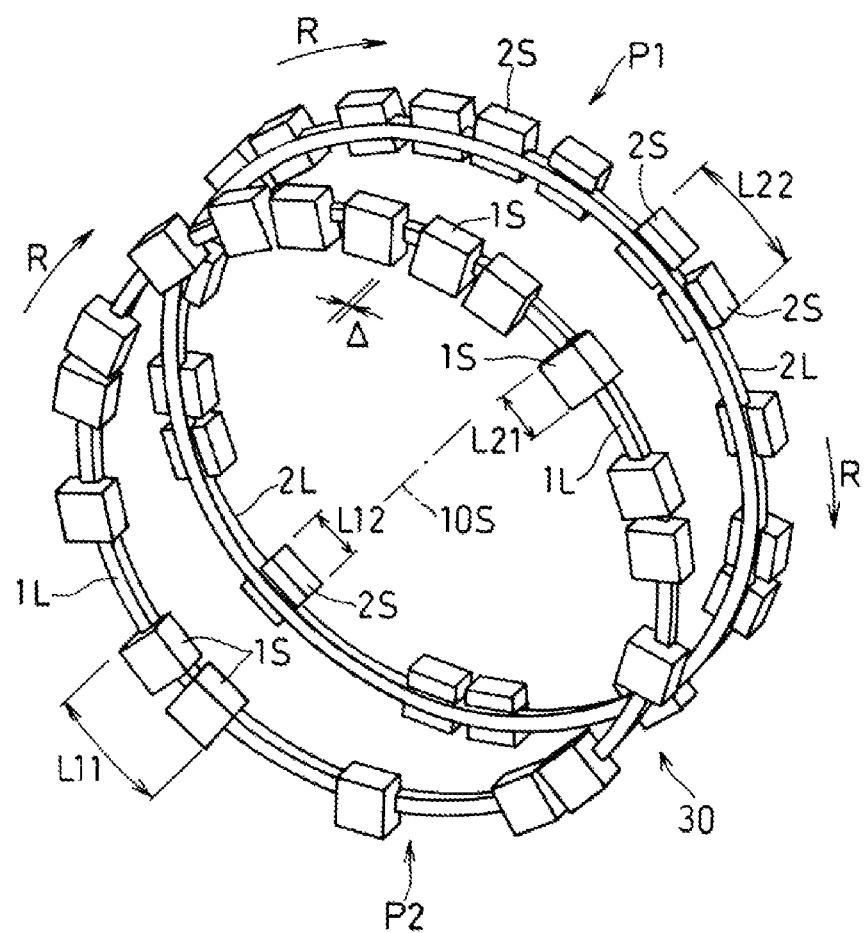

CONVEYING APPARATUS AND METHOD

TECHNICAL FIELD

The present invention relates to conveying apparatus and method that mainly convey a finished article, a half-finished article, a part, or the like of a wearable article while varying the speed thereof.

BACKGROUND ART

This kind of conveying apparatus includes a plurality of pads, and receives workpieces from an upstream side in a reception position by the pads and delivers the workpieces to a downstream side in a delivery position. Variations in pad conveyance speed between the reception and delivery cause variations in the space between the workpieces between the reception position and the delivery position.

This kind of conveying apparatus usually includes a large number of pads that are driven and rotated by a rotating shaft, a supporting ring that is rotatably supported around the rotating shaft and supports the pads in such a way that the pads move in a predetermined orbit, and a guide mechanism that is provided between the pads and the rotating shaft and guides the relative movement of the pads and the supporting ring. A large number of sliders, whose number is the same as that of pads, are mounted on a rail of the guide mechanism so as to be slidable in a circumferential direction. Each slider is guided by the rail and is accelerated and decelerated in the circumferential direction together with the pad by a variable speed mechanism (PTL 1).

CITATION LIST

Patent Literature

PTL 1: WO 2018/011905 (FIG. 4)

SUMMARY OF INVENTION

In order to increase the number of workpieces that are conveyed by this kind of conveying apparatus per unit time, it is necessary to increase the number of articles that can be obtained by the conveying apparatus, that is, the number of pads and the number of sliders. However, an increase in the number of articles that can be obtained by the conveying apparatus causes interference between adjacent sliders; thus, there is an upper limit to the number of pads.

Moreover, the sliders of the guide mechanism guiding the pads are placed in positions closer to an inner circumferential side than the pads. Consequently, the distance between adjacent sliders is smaller than the distance between adjacent pads, which makes the adjacent sliders tend to interfere with each other.

Furthermore, an attempt to narrow the space between the workpieces also causes interference between the sliders.

Therefore, an object of the present invention is to make it possible to increase the number of workpieces that can be conveyed by a conveying apparatus per unit time by narrowing the pitch between workpieces in the conveying apparatus provided with a variable speed mechanism and in a conveying method and thereby support high-speed processing.

In a first aspect, the apparatus of the present invention includes: a rotating shaft 10;

first pads 1 and second pads 2 arranged around the rotating shaft 10, the first and second pads orbiting along an orbit with their speeds being varied, the first and second pads being alternately arranged so as to be adjacent to each other in a circumferential direction R and each holding a workpiece W;

a variable speed mechanism 20 provided for each of the first and second pads, the variable speed mechanism 20 for accelerating and decelerating each of the first and second pads during the orbiting;

a first slider 1S provided for each of the first pads 1 in a different position in an axial direction S of the rotating shaft, the first slider 1S orbiting with the corresponding first pad 1 with speed of the first slider 1S being varied;

a second slider 2S provided for each of the second pads 2 in a different position in the axial direction S of the rotating shaft, the second slider 2S orbiting with the corresponding second pad 2 with speed of the second slider 2S being varied;

a first rail 1L supporting the first pads 1 via the first sliders 1S, the first rail 1L guiding the first sliders 1S and not guiding the second sliders 2S; and a second rail 2L arranged so as to be spaced apart from the first rail 1L and supporting the second pads 2 via the second sliders 2S, the second rail 2L guiding the second sliders 2S and not guiding the first sliders 1S.

In the first aspect, the method of the present invention includes: a step of conveying in which the first and second pads 1 and 2 convey the workpieces W with speeds of the first and second pads 1 and 2 being varied;

a step of accelerating in which circumferential velocities of the first and second pads 1 and 2 are accelerated by the respective variable speed mechanisms 20;

a step of moving and separating in which the first and second pads 1 and 2 move in a state where a distance between the first pad 1 and the second pad 2 is increased and the first pad and the second pad are separated with each other after speeds of the first and second pads increased in the step of accelerating;

a step of decelerating in which the circumferential velocities of the first and second pads 1 and 2 are decelerated by the respective variable speed mechanisms 20; and a step of moving and approaching in which the first slider 1S and the second slider 2S, which have been decelerated in the step of decelerating, overlap each other in a part in the circumferential direction R, which causes the first pad 1 and the second pad 2 to approach each other, and the first pad 1 and the second pad 2 move in this state where the first pad 1 and the second pad 2 have approached each other.

In the first aspects, the first and second pads 1 and 2 are adjacent to each other in the circumferential direction R, and the first sliders are individually provided for the first pads 1 and the second sliders are individually provided for the second pads 2. That is, the first and second sliders are adjacent to each other in the circumferential direction R, are separated from each other in the axial direction S, and overlap each other in a part in the circumferential direction during deceleration. This makes it possible to reduce the pitch between the first and second pads 1 and 2 that are adjacent to each other in the circumferential direction R.

This reduces the pitch between the workpieces held by the pads, which makes it possible to increase the number of workpieces that can be conveyed by the conveying apparatus per unit time and support high-speed processing.

Moreover, it is possible to form each slider so as to be long in the circumferential direction, which stabilizes an orbiting operation of each pad.

In a second aspect, the apparatus of the present invention includes: first pads 1 and second pads 2 arranged around an axis 10S, the first and second pads orbiting along an orbit with their speeds being varied, the first and second pads being alternately arranged so as to be adjacent to each other in a circumferential direction R and each holding a workpiece W;

a first slider 1S and a second slider 2S provided for each of the first and second pads 1 and 2 in different positions with each other in an axial direction S of the axis 10S, the first and second sliders orbiting with the first and second pads 1 and 2 with speeds of the first and second sliders 1S and 2S being varied;

a first rail 1L supporting the first pads 1 or the second pads 2 via the first sliders 1S, the first rail 1L guiding the first sliders 1S and not guiding the second sliders 2S; and a second rail 2L arranged so as to be spaced apart from the first rail 1L, the second rail supporting the first pads 1 or the second pads 2 via the second sliders 2S, the second rail guiding the second sliders 2S and not guiding the first sliders 1S, wherein, for each of the first pads 1, a first contact length L11 by which the first slider 1S is in contact with the first rail 1L is longer than a second contact length L12 by which the second slider 2S is in contact with the second rail 2L, and wherein, for each of the second pads 2, a third contact length L21 by which the first slider 1S is in contact with the first rail 1L is shorter than a fourth contact length L22 by which the second slider 2S is in contact with the second rail 2L.

In the second aspect, the method of the present invention includes: a step in which the first and second pads 1 and 2 convey the workpieces W with speeds of the first and second pads 1 and 2 being varied;

a step of accelerating in which circumferential velocities of the first and second pads 1 and 2 are accelerated;

a step in which the first and second pads 1 and 2 move in a state where a distance between the first pad 1 and the second pad 2 is increased and the first pad and the second pad are separated with each other after speeds of the first and second pads increased in the step of accelerating;

a step of decelerating in which the circumferential velocities of the first and second pads 1 and 2 are decelerated; and a step in which the first slider 1S and the second slider 2S, which have been decelerated in the step of decelerating, overlap each other in a part in the circumferential direction R, which causes the first pad 1 and the second pad 2 to approach each other, and the first pad 1 and the second pad 2 move in this state where the first pad 1 and the second pad 2 have approached each other.

In the second aspect, the first and second sliders provided for each of the first and second pads 1 and 2 that are adjacent to each other in the circumferential direction R are separated from each other in the axial direction S; therefore, the first slider of the first pad and the second slider of the second pad, each having a long contact length by which each slider is in contact with the rail, can overlap each other in a part in the circumferential direction during deceleration. This makes it possible to reduce the pitch between the first and second pads that are adjacent to each other in the circumferential direction.

Thus, as in the case of the first aspect, it is possible to increase the number of workpieces that are conveyed per unit time and support high-speed processing.

Moreover, since the contact length of the first slider of the first pad and the contact length of the second slider of the second pad are long, an orbiting operation of each pad is stabilized.

It is to be noted that the contact length by which the first or second slider is in contact with the rail means the length, from one circumferential end to the other circumferential end, of the first (or second) slider supporting one pad.

BRIEF DESCRIPTION OF DRAWINGS

FIGS. 3A and 3B are schematic plan views showing a pad and a holding base.

FIGS. 4(a), (b), and (c) are schematic front view, sectional view, and rear view, respectively, of a guide mechanism.

FIG. 5(a) is a front view of a variable speed mechanism, FIGS. 5(b) and (c) are longitudinal sectional views showing second and first sliders, respectively, and FIG. 5(d) is a front view showing a part of the guide mechanism 30.

FIG. 7 is a schematic perspective view showing a rail and a slider.

DESCRIPTION OF EMBODIMENTS

Figure 1:
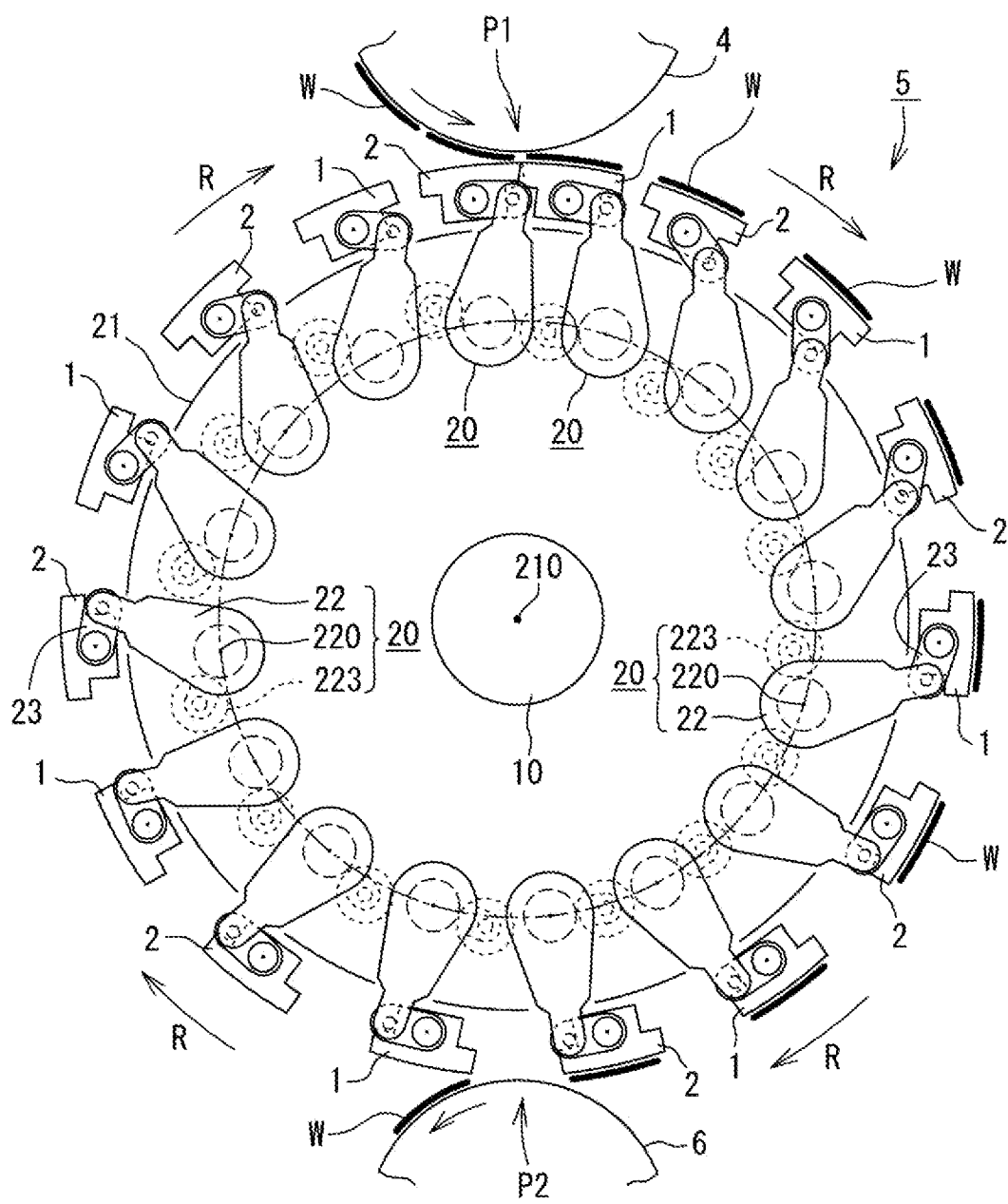
FIG. 1 is a schematic front view of a conveying apparatus showing one embodiment of the present invention.

In the preferred conveying apparatus of the first aspect, the first and second rails 1L and 2L are attached to one supporting ring 3.

In this case, there is no need to provide a supporting ring for each rail.

More preferably, the supporting ring 3 includes a first surface 1F which is one-side surface in the axial direction S and a second surface 2F which is the other-side surface in the axial direction S, and the first rail 1L and the second rail 2L are attached to the first surface 1F and the second surface 2F, respectively.

In this case, a guide mechanism including a supporting ring, a rail, and a slider is likely to be compact.

Preferably, the first rail 1L and the second rail 2L are each formed in a shape of an endless loop.

In this case, the prevision of each rail is high.

Preferably, a pair of the first rails 1L is provided in such a way that the first rails 1L are separated from each other in the axial direction S and a pair of the second rails 2L is provided in such a way that the second rails 2L are separated from each other in the axial direction S, the first sliders 1S are provided for each rail of the first rails 1L, and the second sliders 2S are provided for each rail of the second rails 2L.

In this case, it is possible to support the pad by a pair of rails separated from each other in the axial direction S and the pad is not supported in a cantilever manner, which results in high durability and stability.

Preferably, the conveying apparatus further includes a tubular portion 31 that rotatably supports the rotating shaft, and the supporting ring 3 is rotatably supported on the tubular portion 31.

In this case, the supporting ring 3 rotates with the pads at high speeds and each slider reciprocates in response to variations in speed. This makes each slider and each rail less likely to be worn away and increases durability thereof.

In the preferred conveying method, a step in which the first pads 1 and the second pads 2 receive the workpieces W from an upstream apparatus and the first pads 1 and the second pads 2 deliver the workpieces W to a downstream apparatus in the moving and separating step.

In this case, it is possible to perform what is called a repitch operation that increases the distance between two workpieces which are close to each other.

In the preferred conveying apparatus of the second aspect, for each of the first pads 1, the number of the first sliders 1S is larger than the number of the second sliders 2S, and, for each of the second pads 2, the number of the first sliders 1S is smaller than the number of the second sliders 2S.

In this case, after making the shapes and sizes of the first and second sliders uniform, it is possible to set the first and second sliders so as to have the aforementioned contact length relationship only by a difference in the number of first or second sliders supporting each pad.

For example, each of the first pads 1 may be supported by two first sliders 1S and one second slider 2S and each of the second pads 2 may be supported by one first slider 1S and two second sliders 2S.

More preferably, a first length L1 of each of the first pads 1 in the circumferential direction R is shorter than the first contact length L11 and longer than the second contact length L12, and a second length L2 of each of the second pads 2 in the circumferential direction R is longer than the third contact length L21 and shorter than the fourth contact length L22.

In this case, a slider having a contact length longer than the length of each pad in the circumferential direction achieves stable orbiting of the pad.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Embodiments

Hereinafter, one embodiment of the present invention will be described in accordance with the drawings.

First, an outline of the present manufacturing apparatus will be described.

In FIG. 1, the present manufacturing apparatus includes an upstream roll (an upstream apparatus) 4, a variable speed conveying apparatus 5, and a downstream roll (a downstream apparatus) 6. The variable speed conveying apparatus 5 includes a plurality of first and second pads 1 and 2 alternately in a circumferential direction R. The above-mentioned rolls 4 and 6 and the pads 1 and 2 for holding convey workpieces W.

The pads 1 and 2 for holding rotate along the orbit of the variable speed conveying apparatus 5 with the speeds of the pads 1 and 2 being varied, and receive the workpieces W from the upstream roll 4 in a reception position P1 and deliver the workpieces W onto the downstream roll 6 in a delivery position P2.

Next, the details of a variable speed mechanism 20 of this embodiment will be described. The variable speed mechanism 20 is provided for each of the pads 1 and 2 and accelerates and decelerates each of the pads 1 and 2 while the pads 1 and 2 are orbiting.

As shown in FIG. 1, a plurality of crank arms 22 are arranged on one driving wheel 21 with an equiangular pitch. The space between the crank arms 22 is unchangeable, and arm centers 220, which are the rotation centers of these crank arms 22, rotate with the driving wheel 21 at the same angular speed. The driving wheel 21 rotates with a rotating shaft 10 in the circumferential direction R at a constant angular speed.

Figure 2:
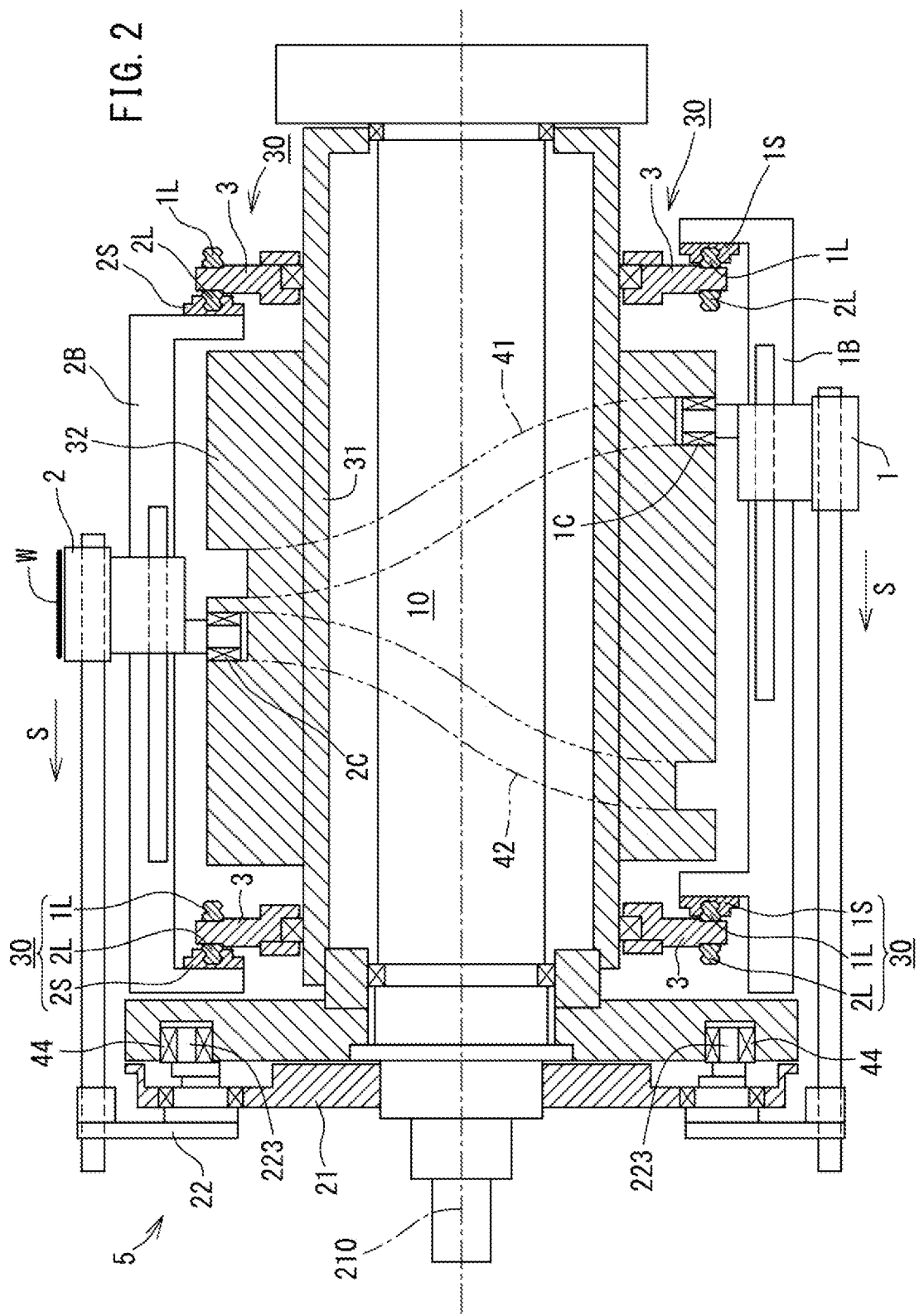
FIG. 2 is a schematic longitudinal sectional view of the conveying apparatus taken along the line 4b-4b of FIG. 4.

A cam roller 223 for varying speed is provided in a position separated from the arm center 220 of each crank arm 22, and the cam roller 223 moves along a cam groove 44 for varying speed of FIG. 2. The cam groove 44 for varying speed is eccentric with respect to a center of drive 210, which is the rotation center of the driving wheel 21, and is immovable. Thus, the distance from the center of drive 210 to the cam roller 223 periodically increases and reduces depending on the positions of the cam roller 223 and the cam groove 44.

Consequently, each crank arm 22 of FIG. 1 periodically swings within a given angular range and the tip of the crank arm 22 periodically swings. That is, in the approximately left half of an area shown in FIG. 1, the tip of each crank arm 22 is displaced from the arm center 220 of the crank arm 22 in a conveyance direction along the circumferential direction R; in the approximately right half of the area shown in FIG. 1, the tip of each crank arm 22 is displaced in an opposite direction.

A link lever 23 pin linked to the tip of each crank arm 22 and each of the first and second pads 1 and 2 pin linked to the link levers 23 are also displaced in conjunction with a swing of the tip of the crank arm 22. Due to the above-mentioned swing of each crank arm 22, the distance between the arm center 220 of the crank arm 22 and each of the pads 1 and 2 varies; therefore, the space between the first pad 1 and the second pad 2 that are adjacent to each other also varies. Consequently, the angular speeds of the first and second pads 1 and 2 for holding and the space between the pads 1 and 2 in the circumferential direction R vary.

Next, a guide mechanism 30 guiding the above-mentioned orbiting of the pads 1 and 2 will be described.

As shown in FIG. 2, the first and second pads 1 and 2 are guided by the guide mechanism 30 along the above-mentioned orbit via first and second bases 1B and 2B, respectively, which are long in an axial direction S. The guide mechanism 30 includes first and second sliders 1S and 2S, first and second rails 1L and 2L, and a supporting ring 3 in the shape of a doughnut-shaped plate, which are shown in FIGS. 2 and 4.

In FIG. 2, the driving wheel 21 integrally rotates with the rotating shaft 10. The rotating shaft 10 is rotatably supported on the inner circumferential side of a tubular portion 31. On the other hand, the supporting ring 3 is rotatably supported on the outer periphery of the tubular portion 31. A driving force of an unillustrated motor may be input to the supporting ring 3 to make the supporting ring 3 rotate at a constant angular speed.

In FIGS. 5(*b*) and (*c*), the first rail 1L and the second rail 2L are attached to a first surface 1F which is one surface of each supporting ring 3 in the axial direction S and a second surface 2F which is the other surface in the axial direction S, respectively. Consequently, the first rail 1L and the second rail 2L are provided so as to be separated from each other in the axial direction S and parallel to each other. Moreover, a pair of first rails 1L is arranged such that the first rails 1L are parallel to each other, and a pair of second rails 2L is also arranged such that the second rails 2L are parallel to each other.

As shown in FIGS. 4(a) and (c), each of the rails 1L and 2L is an endless annular ring (perfect circle). Only the first slider 1S is slidably attached to the first rail 1L of FIG. 4(b). On the other hand, only the second slider 2S is slidably attached to the second rail 2L.

In FIG. 2, the sliders 1S and 2S and the rails 1L and 2L are placed in positions closer to the center of drive 210 than the pads 1 and 2. That is, the orbital paths of the sliders 1S and 2S are located in positions closer to an inner circumferential side than the orbital paths of the pads 1 and 2.

In FIG. 5, the first sliders 1S are provided for the respective first pads 1 in different positions from the second sliders 2S in the axial direction S of the rotating shaft 10 (FIG. 2) and orbit with the first pads 1 with the speeds of the first sliders 1S and the first pads being varied. The second sliders 2S are provided for the respective second pads 2 in different positions from the first sliders 1S in the axial direction S of the rotating shaft 10 (FIG. 2) and orbit with the second pads 2 with the speeds of the second sliders 2S and the second pads being varied. The above-mentioned first rail 1L of FIG. 2 supports the first pads 1 via the first sliders 1S and the first bases 1B, and guides the first sliders 1S and does not guide the second sliders 2S. On the other hand, the second rail 2L supports the second pads 2 via the second sliders 2S and the second bases 2B, and guides the second sliders 2S and does not guide the first sliders 1S.

In the present embodiment, each rail is formed so as to be convex in cross section and each slider is formed so as to be concave in cross section. However, each rail may be formed as a concave groove and each slider may be formed so as to be convex.

In FIG. 2, a cam drum 32 may be fixed to the tubular portion 31. First and second cam grooves 41 and 42 that displace the pads 1 and 2, respectively, in the axial direction S are provided in the cam drum 32.

In FIG. 2, the first and second pads 1 and 2 are attached to the first and second bases 1B and 2B, respectively, in such a way that the first and second pads 1 and 2 can reciprocate in the axial direction S. On the other hand, the first and second pads 1 and 2 include first and second cam followers 1C and 2C fitted into the first and second cam grooves 41 and 42, respectively.

Consequently, the above-mentioned first and second pads 1 and 2 of FIG. 3A separate from each other in the circumferential direction R and also separate from each other in the axial direction S as shown in FIG. 3B while rotating in the circumferential direction R (FIG. 1).

As shown in FIG. 3A, the pads 1 and 2 have roughly triangular shapes facing in opposite directions and can approach each other in the circumferential direction R. Therefore, the first base 1B and the second base 2B of FIG. 3A approach each other in the reception position P1 of FIG. 1, that is, at low speeds.

On the other hand, in the reception position P1, the first and second sliders 1S and 2S of FIGS. 4(a) and (c) are relatively displaced to the extent that a part of the first slider 1S and a part of the second slider 2S overlap each other in the circumferential direction R. This makes it possible to increase the length (size) of each of the sliders 1S and 2S in the circumferential direction R and thereby make stable guidance possible and, at the same time, to reduce the pitch between the above-mentioned pads 1 and 2 of FIG. 1 and thereby increase the number of pads 1 and 2.

This makes high-speed conveyance of small workpieces possible.

Next, a method of variable speed conveyance of the workpieces W of FIG. 1 will be described.

Variable speed conveyance of the workpieces includes the following steps: a conveying step, an accelerating step, a moving and separating step, a decelerating step, and a moving and approaching step.

The first and second pads 1 and 2 of FIG. 1 receive the workpieces W from the upstream roll 4 in the reception position P1 by sucking the workpieces W and making them cling thereto by negative pressure. The first and second pads 1 and 2 that have received the workpieces W perform the step of conveying the workpieces W by orbiting with the speeds of the first and second pads 1 and 2 being varied. Then, after delivering the workpieces W to the downstream roll 6 in the delivery position P2, the first and second pads 1 and 2 of FIG. 1 return to the reception position P1 with the speeds thereof being varied. The following are detailed descriptions of these operations.

In the above-mentioned accelerating stroke (period), the circumferential velocities of the first and second pads 1 and 2 that have received the workpieces W in the reception position P1 are accelerated by the variable speed mechanisms 20. As a result, the speeds of the pads 1 and 2 are gradually increased and the pitch between the first and second pads 1 and 2 that are adjacent to each other is increased; in this way, the moving and separating step is performed.

It is to be noted that the operation and structure of the variable speed mechanism 20 are well known per se and disclosed in, for example, WO 2018/011905, the contents of which are incorporated herein in their entirety.

That is, in the moving and separating step, the first and second pads 1 and 2 holding the workpieces W move and orbit in a state in which the distance between the first pad 1 and the second pad 2, whose speeds were increased by acceleration, is increased.

On the other hand, the first and second pads 1 and 2 separate in the circumferential direction R as shown in FIGS. 3A and 3B by being guided by the first and second cam grooves 41 and 42, respectively, of the cam drum 32 as shown in FIG. 2, and then the distance between the first and second pads 1 and 2 is increased in the axial direction S.

Then, the first and second pads 1 and 2 of FIG. 1 arrive at the delivery position P2 abutting on the downstream roll 6 and deliver the workpieces W held thereby to the downstream roll 6. At the time of this delivery, the circumferential velocities of the pads 1 and 2 may be in any one of the following states: the circumferential velocities of the pads 1 and 2 are being accelerated, the circumferential velocities of the pads 1 and 2 are being increased, and the circumferential velocities of the pads 1 and 2 are constant.

When the workpieces W are delivered in a state in which they are separated in both the circumferential direction R and the axial direction S of FIG. 3 as described above, the workpiece W may be a panel placed in a main body portion of a disposable diaper. A method for placing such a panel is disclosed in WO 2017/056952 A1, for example.

After the above-mentioned delivery, the circumferential velocities of the first and second pads 1 and 2 of FIG. 1 are decelerated by the variable speed mechanisms 20 from the delivery position P2 until arrival at the reception position P1: in this way, the decelerating step is performed. During this deceleration, the first and second pads 1 and 2 approach each other in the axial direction S along the first and second cam grooves 41 and 42 of FIG. 2 and approach each other in the circumferential direction R as shown in FIG. 3A.

When arriving at the reception position P1 in a state in which the first and second pads 1 and 2 of FIG. 1 approach each other in the circumferential direction R, the first and second pads 1 and 2 receive the workpieces W from the upstream roll 4.

In this case, when the workpiece W is small, the pads 1 and 2 of FIG. 3A are also small in the circumferential direction R and the pads 1 and 2 can approach each other. On the other hand, the orbiting of the pads 1 and 2 is guided by the guide mechanism 30 of FIG. 4.

The first and second sliders 1S and 2S of the guide mechanism 30 of FIG. 4 need a certain length in the circumferential direction R in order to stabilize guidance of the pads in the circumferential direction R. Thus, in the reception position P1, the adjacent sliders 1S and 2S overlap each other in the circumferential direction R.

That is, a step is performed in which, in the reception position P1 of FIG. 4, the first slider 1S and the second slider 2S after deceleration overlap each other in a part in the circumferential direction R, which causes the first pad 1 and the second pad 2 of FIG. 5 to approach each other, and the first pad 1 and the second pad 2 move in this state in which they have approached each other. During this step, the first pad 1 and the second pad 2 receive the workpieces W from the upstream roll 4 in the reception position P1.

The reason why this overlapping is made possible is that, in FIG. 5, the first slider 1S of FIG. 5(*c*) guiding the first pad 1 in the circumferential direction R slides on the first rail 1L and the second slider 2S of FIG. 5(*b*) guiding the second pad 2 of FIG. 5(*a*) in the circumferential direction R slides on the second rail 2L. That is, the reason is that, since the first slider 1S and the second slider 2S, which are adjacent to each other, of FIG. 5(*d*) slide on the first and second rails 1L and 2L separated from each other in the axial direction S as shown in FIGS. 5(*b*) and (*c*), they can approach each other in an overlapping state as shown in FIG. 5(*d*).

Incidentally, in the present invention, there is no need for the pads 1 and 2 to move in the axial direction S as shown in FIGS. 3A and 3B. Moreover, the pads 1 and 2 may include mechanisms that make them turn around the normal to a drum after separating in the circumferential direction R. This mechanism is described in, for example, WO 2005/075163, the contents of which are incorporated herein in their entirety.

Moreover, the rails 1L and 2L of FIGS. 5(*b*) and (*c*) may be arranged side by side on the outer circumferential surface of the supporting ring 3, not on the first surface 1F or the second surface 2F of the supporting ring 3.

Furthermore, the pads of the aforementioned embodiment are roughly triangular or pentagonal in shape; they may be square or rectangular in shape.

In addition, the first pad and the second pad may be completely identical in shape.

Moreover, each pad may include, for example, a machining apparatus such as an anvil. Furthermore, each pad may hold the workpiece by sucking the workpiece and making it cling thereto by negative pressure or may hold the workpiece by a needle, a hook, or the like.

Next, another embodiment of the variable speed conveying apparatus 5 will be described.

Figure 6:
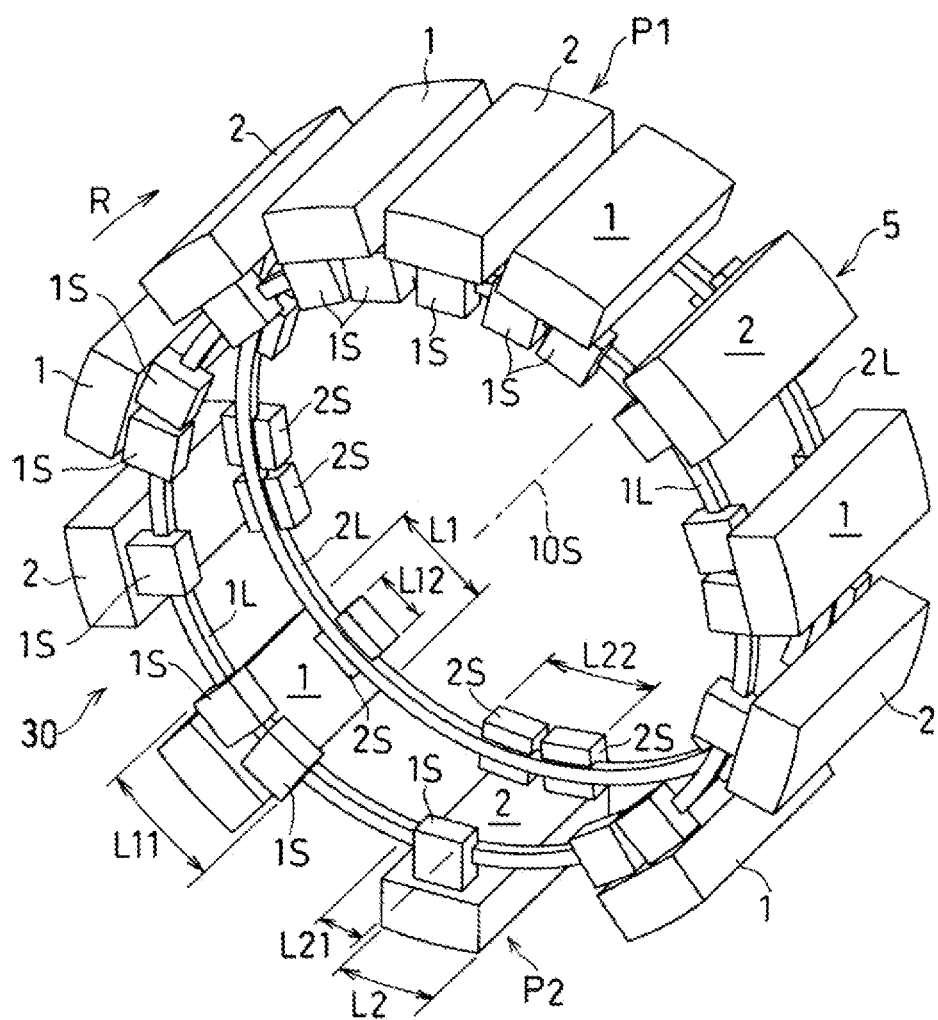
FIG. 6 is a schematic perspective view of a conveying apparatus showing another embodiment of the present invention.

FIGS. 6 and 7 show the variable speed conveying apparatus and the guide mechanism 30, respectively, of the other embodiment.

In FIG. 6, the variable speed conveying apparatus 5 includes a large number of first and second pads 1 and 2, a large number of first and second sliders 1S and 2S, and first and second rails 1L and 2L.

The first and second pads 1 and 2 are arranged around an axis 10S, orbit along an orbit with the speeds thereof being varied, are alternately arranged so as to be adjacent to each other in a circumferential direction R, and convey workpieces while holding them. Also in the present embodiment, as in the case of the aforementioned embodiment, the pads 1 and 2 rotate along the orbit of the variable speed conveying apparatus 5 with the speeds of the pads 1 and 2 being varied, and receive the workpieces (not shown in the drawing) from an unillustrated upstream roll in a reception position P1 and deliver the workpieces (not shown in the drawing) onto a downstream roll in a delivery position P2.

It is to be noted that, also in the present embodiment, the workpiece may be held by being sucked and made to cling to the outer surface of the pad.

Next, the details of the guide mechanism 30 will be described.

The first and second sliders 1S and 2S are provided for each of the first and second pads 1 and 2 in different positions in an axial direction S of the axis 10S and orbit with the first and second pads 1 and 2 with the speeds of the first and second sliders 1S and 2S being varied.

It is to be noted that, as in the case of the aforementioned embodiment, the axis 10S is the axis of the rotating shaft 10 (see FIG. 2).

The first rail 1L supports the first pads 1 or the second pads 2 via the first sliders 1S, and guides the first sliders 1S and does not guide the second sliders 2S. On the other hand, the second rail 2L supports the first pads 1 or the second pads 2 via the second sliders 2S, and guides the second sliders 2S and does not guide the first sliders 1S.

As is clearly shown in FIG. 7, the above-mentioned second rail 2L is arranged so as to be separated from the above-mentioned first rail 1L and parallel thereto. It is to be noted that, as in the case of the above-mentioned embodiment, the rails 1L and 2L are fixed to a supporting ring (not shown in the drawing) that is driven and rotated.

Also in the present embodiment of FIG. 6, as in the case of the aforementioned embodiment, the sliders 1S and 2S and the rails 1L and 2L are placed in positions closer to the axis 10S than the pads 1 and 2. That is, the orbital paths of the sliders 1S and 2S are located in positions closer to an inner circumferential side than the orbital paths of the pads 1 and 2.

As shown in FIG. 6, each first pad 1 is supported by two first sliders 1S and one second slider 2S. On the other hand, each second pad 2 is supported by one first slider 1S and two second sliders 2S.

It is to be noted that the sliders 1S and 2S have the same or symmetrical shape and structure.

As described above, the number of sliders supporting each of the pads 1 and 2 is set; therefore, for each first pad 1, a first contact length L11 by which the first sliders 1S are in contact with the first rail 1L is longer than a second contact length L12 by which the second slider 2S is in contact with the second rail 2L. Moreover, for each second pad 2, a third contact length L21 by which the first slider 1S is in contact with the first rail 1L is shorter than a fourth contact length L22 by which the second sliders 2S are in contact with the second rail 2L.

In FIG. 6, a first length L1 of each first pad 1 mentioned above in the above-mentioned circumferential direction R is shorter than the first contact length L11 and longer than the second contact length L12.

On the other hand, a second length L2 of each second pad 2 in the circumferential direction R is longer than the third contact length L21 and shorter than the fourth contact length L22.

Since the contact lengths L1 to L4 of the sliders 1S and 2S are set for the lengths L1 and L2 of the pads 1 and 2 in this manner, it is possible to prevent adjacent sliders from interfering with each other even when adjacent first pad 1 and second pad 2 approach each other.

On the other hand, it is possible to support the first pad 1 with two first sliders 1S and one second slider 2S, which stabilizes support in the circumferential direction. Moreover, support of the second pad 2 in the circumferential direction is also stabilized in a similar manner.

It is to be noted that two first sliders 1S supporting the first pad 1 may be provided as one first slider 1S which is long in the circumferential direction R. Likewise, two second sliders 2S supporting the second pad 2 may be provided as one second slider 2S which is long in the circumferential direction R.

Next, a method of variable speed conveyance of the workpieces will be described.

Variable speed conveyance of the workpieces includes the following steps: a conveying step, an accelerating step, a moving and separating step, a decelerating step, and a moving and approaching step.

The first and second pads 1 and 2 of FIG. 6 receive the workpieces from the upstream roll in the reception position P1 by sucking the workpieces and making them cling thereto by negative pressure. The first and second pads 1 and 2 that have received the workpieces perform the step of conveying the workpieces by orbiting with the speeds of the first and second pads 1 and 2 being varied. Then, after delivering the workpieces to the downstream roll in the delivery position P2, the first and second pads 1 and 2 return to the reception position P1 with the speeds thereof being varied. The following are detailed descriptions of these operations.

In the above-mentioned accelerating stroke (period), the circumferential velocities of the first and second pads 1 and 2 that have received the workpieces in the reception position P1 are accelerated by variable speed mechanisms 20. As a result, the speeds of the pads 1 and 2 are gradually increased and the pitch between the first and second pads 1 and 2 that are adjacent to each other is increased; in this way, the moving and separating step is performed.

It is to be noted that the operation and structure of the variable speed mechanism 20 are well known per se and disclosed in, for example, WO 2018/011905, the contents of which are incorporated herein in their entirety.

Then, the first and second pads 1 and 2 arrive at the delivery position P2 abutting on the downstream roll and deliver the workpieces held thereby to the downstream roll. At the time of this delivery, the circumferential velocities of the pads 1 and 2 may be in any one of the following states: the circumferential velocities of the pads 1 and 2 are being accelerated, the circumferential velocities of the pads 1 and 2 are being increased, and the circumferential velocities of the pads 1 and 2 are constant.

After the above-mentioned delivery, the circumferential velocities of the first and second pads 1 and 2 are decelerated by variable speed mechanisms, which are similar to those described above, from the delivery position P2 until arrival at the reception position P1; in this way, the decelerating step is performed. During this deceleration, the first and second pads 1 and 2 approach each other in the circumferential direction R.

When arriving at the reception position P1 in a state in which the first and second pads 1 and 2 approach each other in the circumferential direction R, the first and second pads 1 and 2 receive the workpieces from the upstream roll.

A step is performed in which, in the reception position P1 of FIG. 7, the first slider 1S and the second slider 2S after deceleration overlap each other in a part A in the circumferential direction R, which causes the first pad 1 and the second pad 2 of FIG. 6 to approach each other, and the first pad 1 and the second pad 2 move in this state in which they have approached each other. During this step, the first pad 1 and the second pad 2 receive the workpieces from the upstream roll in the reception position P1.

The reason why this overlapping is made possible is that, in FIG. 6, the first slider 1S guiding the first pad 1 in the circumferential direction R slides on the first rail 1L and the second slider 2S guiding the second pad 2 in the circumferential direction R slides on the second rail 2L. That is, the reason is that, since the first slider 1S and the second slider 2S of FIG. 7 that move in parallel to each other slide on the first and second rails 1L and 2L separated from each other in the direction of the axis 10S, the first slider 1S and the second slider 2S can approach each other in a state in which they overlap each other in the circumferential direction R.

While the preferred embodiments have been described above with reference to the drawings, a person skilled in the art would easily conceive of various changes and modifications based on the description within the scope obvious to the person skilled in the art.

For example, there is no need for the supporting ring to rotate in synchronization with the rotating shaft. Moreover, a supporting member which is not continuous in a circular fashion may be adopted in place of the supporting ring.

The speed of each pad may be constant in the reception position from the start to end of reception.

The upstream apparatus and the downstream apparatus may be conveyors and the like, not rolls.

Therefore, these changes and modifications are construed as being included in the scope of the present invention defined by the claims.

Industrial Applicability

In addition to finished articles of various absorbent articles such as disposable pants and diapers, the present invention can be used in conveyance in the manufacture of parts and half-finished articles of these absorbent articles.

REFERENCE SIGNS LIST

1: first pad
2: second pad
1B: first base
2B: second base
1C: first cam follower
2C: second cam follower
1S: first slider
2S: second slider
1L: first rail
2L: second rail
1F: first surface
2F: second surface
10: rotating shaft
10S: axis
20: variable speed mechanism
21: driving wheel
210: center of drive
22: crank arm
220: arm center
223: cam roller
23: link lever
3: supporting ring
30: guide mechanism 31: tubular portion
32: cam drum
4: upstream roll (apparatus)
5: variable speed conveying apparatus
6: downstream roll (apparatus)
41: first cam groove
42: second cam groove
44: cam groove for varying speed
P1: reception position
P2: delivery position
R: circumferential direction
S: axial direction
W: workpiece
L1: first length
L2: second length
L11, L12, L21, L22: first to fourth contact lengths

The invention claimed is:

1. A conveying apparatus comprising:
a rotating shaft;
first pads and second pads arranged around the rotating shaft, the first and second pads orbiting along an orbit with their speeds being varied, the first and second pads being alternately arranged so as to be adjacent to each other in a circumferential direction and each holding a workpiece;
a variable speed mechanism provided for each of the first and second pads, the variable speed mechanism for accelerating and decelerating each of the first and second pads during the orbiting;
a first slider provided for each of the first pads, the first slider orbiting with the corresponding first pad with speeds of the first slider and the corresponding first pad being varied;
a second slider provided for each of the second pads in a different position from the first slider in an axial direction of the rotating shaft, the second slider orbiting with the corresponding second pad with speeds of the second slider and the corresponding second pad being varied;
a first rail supporting the first pads via the first sliders, the first rail guiding the first sliders and not guiding the second sliders; and
a second rail arranged so as to be spaced apart from the first rail and supporting the second pads via the second sliders, the second rail guiding the second sliders and not guiding the first sliders.

2. The conveying apparatus according to claim 1,
wherein the first rail and the second rail are attached to one supporting ring.

3. The conveying apparatus according to claim 2,
wherein the one supporting ring comprises a first surface which is one-side surface in the axial direction and a second surface which is another-side surface in the axial direction, and
wherein the first rail is attached to the first surface and the second rail is attached to the second surface.

4. The conveying apparatus according to claim 2,
wherein the first rail and the second rail are each formed in a shape of an endless loop.

5. The conveying apparatus according to claim 1,
wherein a pair of the first rails is provided in such a way that the first rails are separated from each other in the axial direction and a pair of the second rails is provided in such a way that the second rails are separated from each other in the axial direction,
wherein the first sliders are provided for the respective first rails, and
wherein the second sliders are provided for the respective second rails.

6. The conveying apparatus according to claim 2, further comprising:
a tubular portion that rotatably supports the rotating shaft,
wherein the supporting ring is rotatably supported on the tubular portion.

7. A method for conveying the workpieces using the conveying apparatus according to claim 1, comprising:
a step of conveying in which the first and second pads convey the workpieces with speeds of the first and second pads being varied;
a step of accelerating in which circumferential velocities of the first and second pads are accelerated by the respective variable speed mechanisms;
a step of moving and separating in which the first and second pads move in a state where a distance between the first pad and the second pad is increased and the first pad and the second pad are separated with each other after speeds of the first and second pads increased in the step of accelerating;
a step of decelerating in which the circumferential velocities of the first and second pads are decelerated by the respective variable speed mechanisms; and
a step of moving and approaching in which the first slider and the second slider, which have been decelerated in the step of decelerating, overlap each other in a part in the circumferential direction, which causes the first pad and the second pad to approach each other, and the first pad and the second pad move in this state where the first pad and the second pad have approached each other.

8. The conveying method according to claim 7, comprising:
a receiving step in which the first pads and the second pads receive the workpieces from an upstream apparatus in the step of moving and approaching; and
a delivering step in which the first pads and the second pads deliver the workpieces to a downstream apparatus in the step of moving and separating.

9. A conveying apparatus comprising:
first pads and second pads arranged around an axis, the first and second pads orbiting along an orbit with their speeds being varied, the first and second pads being alternately arranged so as to be adjacent to each other in a circumferential direction and each holding a workpiece;
a first slider and a second slider provided for each of the first and second pads in different positions with each other in an axial direction of the axis, the first and second sliders orbiting with the first and second pads with speeds of the first and second sliders and the first and second pads being varied;
a first rail supporting the first pads or the second pads via the first sliders, the first rail guiding the first sliders and not guiding the second sliders; and
a second rail arranged so as to be spaced apart from the first rail, the second rail supporting the first pads or the second pads via the second sliders, the second rail guiding the second sliders and not guiding the first sliders,
wherein, for each of the first pads, a first contact length by which the first slider is in contact with the first rail his longer than a second contact length by which the second slider is in contact with the second rail, and
wherein, for each of the second pads, a third contact length by which the first slider is in contact with the first rail is shorter than a fourth contact length by which the second slider is in contact with the second rail.

10. The conveying apparatus according to claim 9,
wherein, for each of the first pads, the number of the first sliders is larger than the number of the second sliders, and
wherein, for each of the second pads, the number of the first sliders is smaller than the number of the second sliders.

11. The conveying apparatus according to claim 10,
wherein each of the first pads is supported by two of the first sliders and one of the second slider, and
wherein each of the second pads is supported by one of the first slider and two of the second sliders.

12. The conveying apparatus according to claim 9,
wherein a first length of each of the first pads in the circumferential direction is shorter than the first contact length and longer than the second contact length, and
wherein a second length of each of the second pads in the circumferential direction is longer than the third contact length and shorter than the fourth contact length.

13. A method for conveying the workpieces using the conveying apparatus according to claim 9, comprising:
a step in which the first and second pads convey the workpieces with speeds of the first and second pads being varied;
a step of accelerating in which circumferential velocities of the first and second pads are accelerated;
a step in which the first and second pads move in a state where a distance between the first pad and the second pad is increased and the first pad and the second pad are separated with each other after speeds of the first and second pads increased in the step of accelerating;
a step of decelerating in which the circumferential velocities of the first and second pads are decelerated; and
a step in which the first slider and the second slider, which have been decelerated in the step of decelerating, overlap each other in a part in the circumferential direction, which causes the first pad and the second pad to approach each other, and the first pad and the second pad move in this state where the first pad and the second pad have approached each other.

14. The conveying apparatus according to claim 2,
wherein a pair of the first rails is provided in such a way that the first rails are separated from each other in the axial direction and a pair of the second rails is provided in such a way that the second rails are separated from each other in the axial direction,
wherein the first sliders are provided for the respective first rails, and
wherein the second sliders are provided for the respective second rails.

15. The conveying apparatus according to claim 3,
wherein a pair of the first rails is provided in such a way that the first rails are separated from each other in the axial direction and a pair of the second rails is provided in such a way that the second rails are separated from each other in the axial direction,
wherein the first sliders are provided for the respective first rails, and
wherein the second sliders are provided for the respective second rails.

16. The conveying apparatus according to claim 4,
wherein a pair of the first rails is provided in such a way that the first rails are separated from each other in the axial direction and a pair of the second rails is provided in such a way that the second rails are separated from each other in the axial direction,
wherein the first sliders are provided for the respective first rails, and
wherein the second sliders are provided for the respective second rails.

* * * * *